United States Patent
Randall et al.

(10) Patent No.: US 9,562,832 B2
(45) Date of Patent: Feb. 7, 2017

(54) METHOD OF MEASURING WEAR RATE IN RUBBER TIRES

(71) Applicant: Bridgestone Corporation, Tokyo (JP)

(72) Inventors: Amy M. Randall, Akron, OH (US); Edward D. Kelley, Tallmadge, OH (US); Nicole Capitos-Davis, Akron, OH (US); Sheel P. Agarwal, Solon, OH (US)

(73) Assignee: Bridgestone Corporation, Tokyo (JP)

( * ) Notice: Subject to any disclaimer, the term of this patent is extended or adjusted under 35 U.S.C. 154(b) by 286 days.

(21) Appl. No.: 14/172,561

(22) Filed: Feb. 4, 2014

(65) Prior Publication Data

US 2014/0245812 A1 Sep. 4, 2014

Related U.S. Application Data

(60) Provisional application No. 61/761,024, filed on Feb. 5, 2013.

(51) Int. Cl.
*G01N 3/56* (2006.01)
*G01M 17/02* (2006.01)
*B60C 11/24* (2006.01)
*B24B 5/36* (2006.01)

(52) U.S. Cl.
CPC ............ *G01M 17/027* (2013.01); *B24B 5/366* (2013.01); *B60C 11/246* (2013.04); *G01M 17/022* (2013.01); *G01N 3/56* (2013.01)

(58) Field of Classification Search
CPC ....... G01M 17/022; G01M 17/02; G01M 3/56
USPC .................................................. 73/7–8, 146
See application file for complete search history.

(56) References Cited

U.S. PATENT DOCUMENTS

| | | | |
|---|---|---|---|
| 3,899,917 A * | 8/1975 | Kisbany | G01N 3/56 451/254 |
| 4,995,197 A | 2/1991 | Shieh et al. | |
| 6,050,876 A * | 4/2000 | Ouyang | G01M 17/022 451/254 |
| 6,369,353 B1 | 4/2002 | Soska | |
| 6,412,330 B1 * | 7/2002 | Dicello | G01N 3/56 73/7 |
| 6,609,417 B1 | 8/2003 | Cantu et al. | |

(Continued)

FOREIGN PATENT DOCUMENTS

JP 2011-174821 A 9/2011

OTHER PUBLICATIONS

Ahn, Jae Yul, International Search Report with Written Opinion from PCT/US2014/014669 (11 pp.).

*Primary Examiner* — Peter Macchiarolo
*Assistant Examiner* — Anthony W Megna Fuentes
(74) *Attorney, Agent, or Firm* — Meredith E. Hooker; Harry J. Gwinnell (57) ABSTRACT

A method of measuring wear rate in an actual rubber tire. A section of rubber is cut out of an actual tire below the surface of the tire. The cut out section is attached to the surface of a first wheel. An abrasive substance is attached to the surface of a second wheel. The two wheels are rotated for a predetermined time, in opposite directions, in contact with each other, at uneven rates resulting in some slippage between the surfaces of the two wheels. The wear rate of the rubber tire is measured based on the changes in the cut section over time, in much less time and using less resources than required by conventional wear measurement methods.

13 Claims, 5 Drawing Sheets

(56) References Cited

U.S. PATENT DOCUMENTS

| | | | |
|---|---|---|---|
| 2006/0156790 A1* | 7/2006 | Bocquillon | B60C 11/24 73/8 |
| 2010/0000310 A1* | 1/2010 | Braghiroli | G01B 11/22 73/146 |
| 2012/0186324 A1 | 7/2012 | Neugebauer et al. | |
| 2013/0036790 A1* | 2/2013 | Hirayama | G01N 3/56 73/8 |

* cited by examiner

Original Optical Wear Pattern

40min, 4000g @ 10%Slip

Fig. 4

Original Optical Wear Pattern     40min, 4000g @ 10%Slip

Fig. 5

Original Optical Wear Pattern

40min, 4000g @ 10%Slip

Fig. 6

METHOD OF MEASURING WEAR RATE IN RUBBER TIRES

CROSS-REFERENCE TO RELATED APPLICATIONS

The present U.S. Non-Provisional Application claims the benefit of U.S. Provisional Application No. 61/761,024 filed Feb. 5, 2013, the disclosure of which is expressly incorporated by reference herein in its entirety.

TECHNICAL FIELD

The field of art to which this invention generally pertains is a measurement system for the detection of wear or deterioration.

BACKGROUND

In order to continually improve the properties of tires, it is necessary to measure their performance. An obvious way to measure the performance of a tire is to observe the wear data after normal operation and use. However, since tires now perform for tens of thousands of miles, the length of time required to observe this performance can be very long. As a result, alternatives to accelerate this time frame, while controlling the resource costs, are continually being sought after.

Driving a vehicle continually around a track for an extended period of time (for example, four weeks or more) can produce time-accelerated wear data much faster than the normal running of a vehicle. While this does represent a significant reduction over measuring wear during normal vehicle operation, it still represents an extended period of time, and does require significant resources, e.g., vehicles and drivers.

Similarly, indoor simulations of the outdoor tests, for example, running a mounted tire against a belt or drum for a set period of time, has also been used. This can not only reduce the time required to obtain useful wear data down to a week or less, but clearly reduces the costs associated with driving around a track.

On a laboratory scale, another indoor test which has been used in the past is the use of Lambourn-type machinery. This test requires molding a tire rubber composition into a small wheel or disk, which is then run against a larger, abrasive wheel. While this method similarly reduces the time required to generate wear data, the data must be analyzed closely, since it is not rubber from an actual tire.

Accordingly, there is a continuous search for ways to generate wear data which reduces both testing time, materials and resources, while at the same time improving the correlation of test data with normal vehicle-tire operation and use.

BRIEF SUMMARY OF THE INVENTION

A method of measuring wear rate in a rubber tire is described. A section of rubber is cut out of the tire below the surface of the tire. The section is attached to the surface of a first wheel having an axis, and attaching an abrasive substance to the surface of a second wheel having an axis. The two wheels are rotated under a load normal to the axes of the two wheels for a predetermined time, in opposite directions, in contact with each other, at uneven velocities. The result is slippage between the surfaces of the two wheels and wear including a wear pattern in the rubber section of the tire. The wear rate of the rubber section of the tire is measured based on changes in the section over time.

Embodiments of the invention include: the method described above where optical images of the wear pattern of the tire section are periodically taken after wheel rotation and compared with optical images of the wear pattern of whole tires to match the wear patterns of the tire section and the whole tire; the method described above where the time of rotation is stopped when the wear pattern of the section matches the wear pattern of the whole tire; the method described above where the rotation is stopped at about 40 minutes; the method described above where the optical images are taken at about 10 minute intervals; the method described above where the slippage is up to about 70%; the method described above where the slippage is about 10%; the method described above where the ratio of diameter of first wheel to second wheel is about 3/1 to about 6/1; the method described above where the ratio is about 3.5/1; the method described above where the ratio is about 5.3/1; the method described above where the load is about 500 grams to about 8 kilograms; the method described above where the load is about 4 kilograms; the method described above where the width of the wheels is about 8 mm to about 5 cm; the method described above where the first wheel is about 173 mm in diameter and about 22 mm in width; the method described above where the second wheel is about 49 mm in diameter and about 8.5 mm in width; the method described above where the two wheels are rotated for approximately 40 minutes; the method described above where the wheels are rotated under a normal load of approximately 4000 g; the method described above where the wheels are rotated at uneven rates resulting in slippage between the surfaces of the two wheels of about 10%; the method described above where the wear rate of the rubber tire is measured based on the formula $\Delta W/T$, where T=time, $\Delta W = \rho \times \Delta V$, $\rho$=density of the section, $\Delta V = L \times W \times \rho \times \Delta H$, L=length of the section, W=width of the section, $\Delta H$=thickness of the section before abrasion−thickness of the section after abrasion.

DETAILED DESCRIPTION OF THE INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

Wear rate according to the present invention is measured in terms of change in volume, converted to change in weight, over time. So regardless of the units of weight selected, or the time of measurement, the wear rates will be consistent and comparable. Typically, the weight will be measured in milligrams, and the time in minutes.

Since the rubber being tested is taken right from the tire, any rubber compound conventionally used in tires can be tested. Currently, these are typically styrene-butadiene based rubber compounds having densities ranging anywhere from 0.8 to 1.6 grams/cubic centimeter, and more typically 0.9 to 1.2 grams/cubic centimeter.

Figure 1:
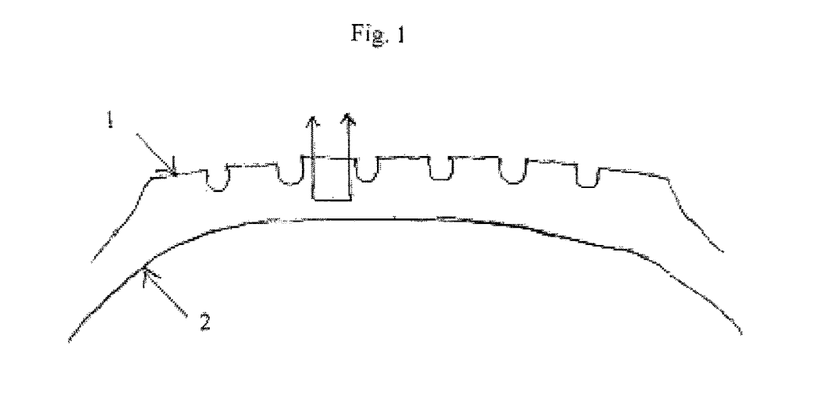
FIG. 1 shows a typical tire tread section tested.

While the larger wheel designed to hold the rubber section cut from the tire can be any manageable size to obtain measurable results, the wheels typically range in a size ratio of 3/1 to 6/1, big to small, such as wheels having ratios of 3.18, 3.53, 3.88, 4.79, 5.32 and 5.85 to 1. For example, a large wheel with a diameter of 173 centimeters (cm) and a small wheel having a diameter of 49 cm would have a ratio of 3.53; and a large wheel with a diameter of 25 cm used with a small wheel with a diameter of 4.7 cm would have a ratio of 5.32. Similarly, with respect to the widths of the wheel, the widths can be any manageable size capable of generating measurable results, but are typically about 8 millimeters (mm) to about 5 cm in width, and more typically about 8.5 mm to about 40 mm in width. Accordingly, the size of the sample attached to the wheel would similarly vary in size to match the respective size of the wheel. The sample section of the tread to be tested is typically cut just below the surface of the tire, so that the surface being tested is that between the surface of the tire and the reinforcement layer or sub-tread (see, e.g., FIG. 1). This helps to produce consistency in comparative test results from one tire to the next, independent of tread pattern. The thickness of the sample should be thick enough to be securely attached to the wheel and thick enough so that meaningful change in thickness data can be generated. Typically the samples are 1 millimeter (mm) to 10 mm thick, more typically 2 mm to 5 mm, and most typically about 3.5 mm thick.

Both the rubber sample cut from the tire and the abrasive material are attached to their respective wheels by any method which will attach them securely, i.e., prevent any slippage of the sample or the material on their respective wheels. This can include conventional mechanical fastening, the use of adhesive laminates such as various commercially available tapes (such as 3M® double sided stick tapes), and conventional adhesives (such as Loctite® Super Glues). In the case of the rubber sample, Super Glues have been found to work well, and in the case of the abrasive sheet material, two sided adhesive tape works well.

The abrasive material can be any abrasive which will successfully remove a measureable amount of rubber from the sample in a reasonable period of time. While the abrasive can be glued or otherwise attached directly to the smaller wheel, for cost and convenience, it is preferred to use abrasive coated or laminated on a substrate such as paper or flexible plastic. This allowed continued and repeated use of the smaller wheel for additional testing without extensive cleaning or disposal of the wheel, and also allows for a wide variety of abrasive materials to be used. Conventional sand paper is typically used, attached with conventional two-sided tape, and the 3M® Safety-Walk™ products with abrasive on one side of the substrate and adhesive on the other side also work well.

The larger wheel should be large enough to support a rubber sample of sufficient size to give meaningful change in weight numbers. The advantage of both normal vehicle testing and track testing is the entire tire has been able to be tested. Part of the problem with the smaller sample, shorter time testing methods in the past is the smaller sample size does not always reflect what is actually happening with the larger tire—which is not true with the present test method described herein. However, in order to obtain this accuracy, the larger wheel must be large enough to hold a sample which when abraded, can provide sufficient data for meaningful calculations. Accordingly, the larger wheels are typically about 20 to about 200 cm in diameter and typically about 5 to about 50 mm wide (see also, ratio description above).

The smaller wheel should be large enough to support a meaningful amount of abrasive material for testing purposes, and provide the necessary slippage for testing, in a reasonable amount of time with the test accuracy required. Typically these wheels are about 3 cm to about 60 cm in diameter (within the ratios described above) and a width at least as wide as the larger wheel containing the sample, and typically about 6 mm to about 10 mm, and most typically about 8 mm in width.

While the smaller wheel can be made of abrasive material in total, for cost and efficiency reasons, this is not preferred. Typically both the larger and smaller wheels are made of metal, with aluminum and stainless steel materials working particularly well. Both wheels can be solid disks of metal, or hollow disks with appropriate wall thicknesses or internal reinforcement to avoid any shape changes during testing. As with the smaller wheel, aluminum and stainless steel work particularly well for the larger wheel as well. For weight saving purposes, the wheels can also be wider at their surfaces and narrower below the surface section, and/or have hole punched in the internal diameter, again to save weight, as long as the surfaces are wide enough to hold samples of abrasive and tire sections to be tested. Lambourn-type machinery manufactured by Iwamoto Seisakusho Co. Ltd. modified as described herein has been found to be useful with the present invention (see *Rubber World*, 151, (6) 79 (1965), the disclosure of which is incorporated by reference).

In order to accelerate the time required to obtain the wear test data, the two wheels are typically forced together under a load applied in a direction normal to the axes of the two wheels. The wheels according to the present invention are typically run along a horizontal axis, but regardless, the load should be applied in a direction normal to the axes of the two wheels to provide adequate abrasion of the tire section in a reasonable amount of time. This load is typically 500 grams to about 8 kilograms (kg), more typically 3 kg to 5 kg, with 4 kg most typically used, and applied using conventional weights. The greater the weight applied, the less time for testing required.

The typical speed that the larger wheel will be run at will depend on the speed the smaller wheel is running at, and vice versa, and the slip ratio desired (e.g., see the slippage discussion below). Typically these speeds range from about 10 to about 400 revolutions per minute (rpm) for either wheel, typically about 10 to about 75 rpm for the larger wheel, and more typically about 20 to about 50 rpm, and typically about 100 rpm to about 300 rpm for the smaller wheel and more typically about 200 rpm, all depending on the slippage ratio desired. At these rpm ratings, the time for a typical test will range from about 30 or 40 minutes to about an hour to obtain useful data, depending, as mentioned above on the rpms, weight applied, and slip ratio. However, the time of testing to obtain the most accurate results, reflecting actual road tire wear, is determined by the observation of the wear pattern, as described below.

For improved accuracy of the test, the visual (scanning electron microscope or optical microscopic) observation of the wear pattern helps determine how long the wear test should be run for optimum accuracy. Either the Steroscan or Olympus microscopes described below or other commercially available microscopes can be used for this purpose. By comparing the wear pattern of the present process to that from conventional whole tire road and belt testing, such as the normal operation of the vehicle or any of the other conventional outdoor or indoor tests, the variable parameters allowable for use with the apparatus described herein, such as wheel rotation speed, time of testing, slip ratios, etc. can be established. This observation is a visual observation as described below, and is done periodically as the abrasion test proceeds, for example, every 10 minutes. See, for example, FIGS. 3, 4 and 5. A close match of the wear pattern of the conventional tests to set the parameters of the test described herein will result in more accurate data for predicting wear characteristics going forward.

It also should be noted that while conventional talc (used typically for cooling purposes with laboratory testing) could be used with the present process, it is preferable to run the tests described without talc. The amount of slippage used between the wheels is that sufficient to produce a measurable amount of wear within a relatively short period of time. The slippage which is required to generate wear will obviously depend on the difference in rpm's of the two wheels, and reasonably can be anything up to 70% percent, and is typically about 5% to about 70%.

As stated above, the amount of loss of rubber during testing is measured optically using conventional optical measurement software, such as Cambridge Steroscan 360 SEM operating with conventional software useful for this purpose, such as Oxford INCA software at 40× magnification. Knowing the density of the material, and the volume removed, the weight can be easily calculated.

Example 1

Seven commercial tires (A through G) were selected from a variety of commercial tire manufacturers. A summary of the tires, their tread design, their construction, and the projected wear mileage from a 4,500 mile tire on a drum wear test is shown in the Table 1. The indoor wear results are influenced by rubber material properties as well as tire design and construction properties. The tire tread abrasion pattern after the indoor wear test was captured by optical and SEM (Scanning Electron Microscope) micrographs. The goal of the current method is to remove the tread rubber component from the tire to determine the tread wear patterning (Example 1) and wear rate (Example 2) from the rubber material independent of the tire design and construction. Furthermore, the method has been developed to more closely correlate actual tire mileage projections to tread material wear patterning and wear rate.

TABLE 1

| Tire | Projected Miles | Construction | Tread Design |
|------|-----------------|--------------|--------------|
| A | 41,055 | 2P + 2S + 1cap + 1strip | High Performance |
| B | 36,959 | 1P + 2S + 1strip | All-season |
| C | 36,538 | 1P + 2S + 2strip | High Performance |
| D | 35,278 | 2P + 2S + 1cap + 1 strip | Touring |
| E | 33,940 | 1P + 2S | Touring |
| F | 31,507 | 2P + 2S + 1cap + 1 strip | High Performance |
| G | 26,613 | 2P + 2S + 1cap + 1 strip | Touring |

Figure 2:
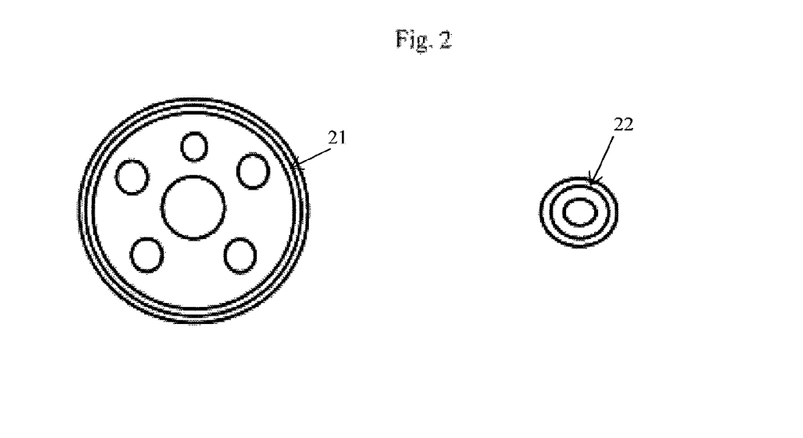
FIG. 2 shows typical test wheels.

P = number of fabric plies
S = number of steel belts
cap = fabric over full length of steel belt
strip = fabric over edge of steel belt Due to the variety of tire construction types and different tread designs, it is difficult to separate the contribution of just the tread material to the overall wear performance. Therefore, this test procedure was developed. In this particular example, the test machine was a Lambourn type machine manufactured by Iwamoto Seisakusho Co. Ltd., modified to work as described herein. First, the tread material was cut from the tire sections at a point below the tire surface (1 in FIG. 1) but above the subtread (2 in FIG. 1). Then the tread material was adhered to a large Lambourn type wheel (21 in FIG. 2) with a diameter of 173 millimeters (mm) and a width of 22 mm using double-sided stick tape. Next an abrasive sandpaper surface (3M® 248D Three-M-Ite Resin Bond PSA Rolls) was adhered to a smaller wheel (22 in FIG. 2) having a diameter of 49 mm, and a width of 8.5 mm. The test procedure did not use any talc and was run at a 10% slip angle. Based on the optical imaging described herein, the testing time and the normal load were found to be optimized at 40 minutes and 4000 g, respectively. The wheel was stopped periodically and optical microscope images were taken of the wear pattern on the tread surface. The treads were optically imaged on an Olympus SZH Stereomicroscope with a 60× objective typically using QCapture Pro software to capture the picture.

Figure 3:
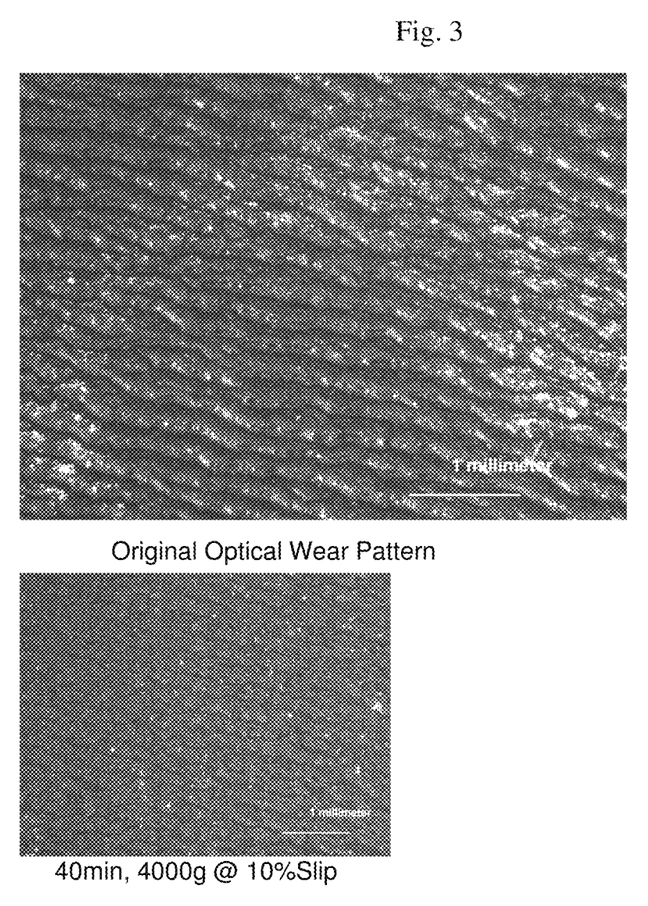
FIGS. 3, 4 and 5 shows typical tire wear patterns.
Figure 4:
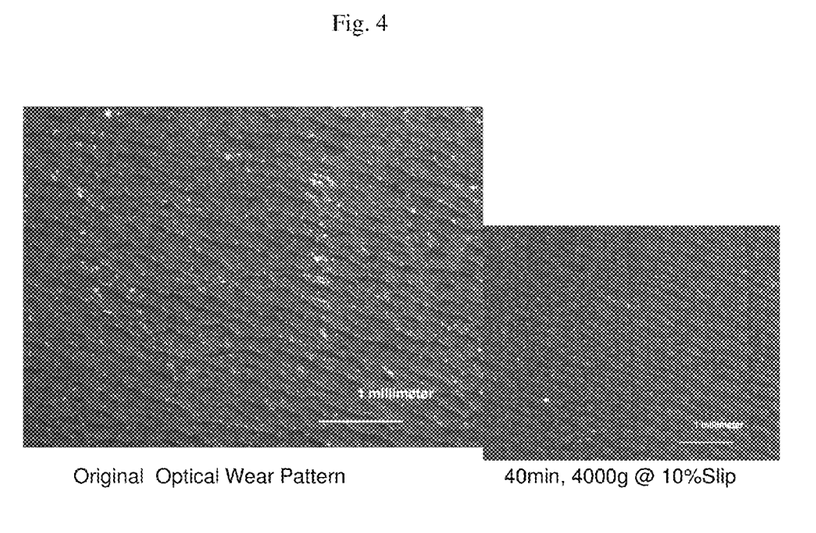
Figure 5:
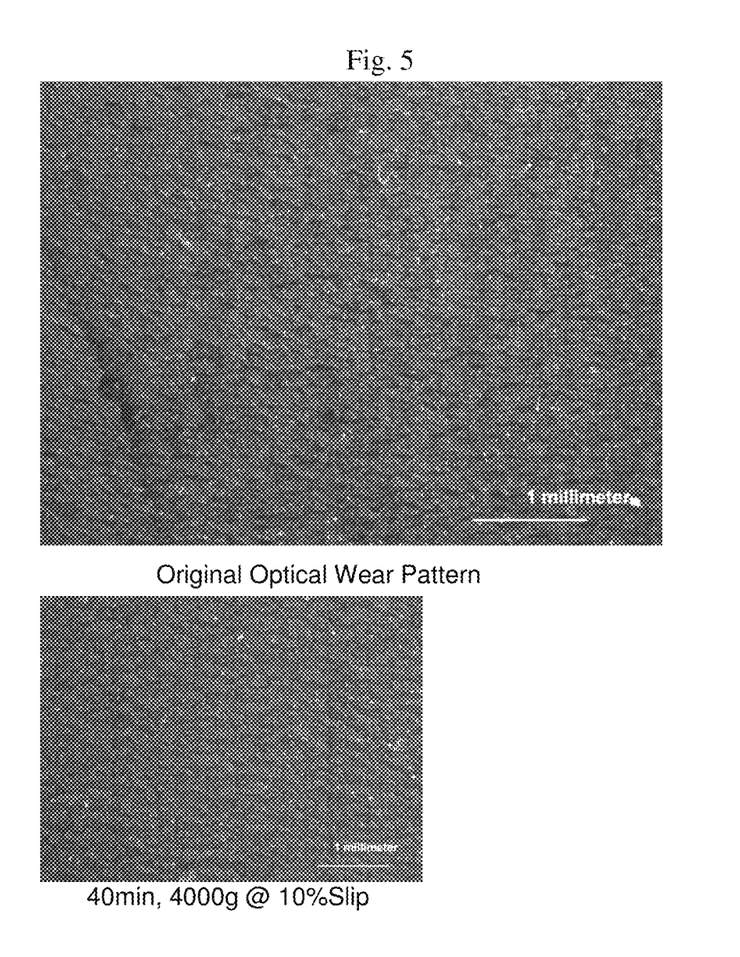

FIGS. 3, 4 and 5 are comparative pictures of the conventional indoor wear abrasion pattern and of the test pattern at the test conditions of the present invention described above. The test materials shown in the pictures correspond to commercial tire samples E, B and A respectively, shown in Table 1 below. The material wear pattern is very pronounced after indoor testing for each of the tire treads, and the optimized test method according to the present invention is able to reproduce the wear pattern without the influence of tire construction or tread design.

TABLE 2

| Tire | Indoor Test Mileage Rating | Wear Pattern Reproduced |
| --- | --- | --- |
| A | 1 | Yes |
| B | 2 | Yes |
| C | 3 | Yes* |
| D | 4 | Yes |
| E | 5 | Yes* |
| F | 6 | Yes |
| G | 7 | Yes |

*substantially reproduced

Example 2

Figure 6:
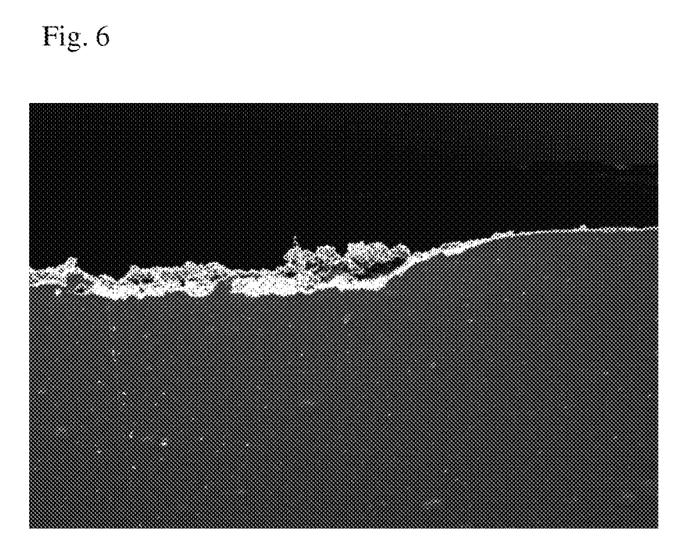
FIG. 6 shows typical tread optical imaging after testing.

For this example, a series of 4 different tire treads (H to K) were prepared and evaluated using the test method described in Example 1 above. The basic rubber compounding formulation of the tires included those typically found in tires including styrene butadiene rubber (SBR), natural rubber, silica and carbon black fillers, oil, processing aids, sulfur, accelerators, and zinc oxide. Each experimental compound used a different type of SBR varying in microstructure, glass transition temperature, and molecular weight. In this example, the experimental tires were all Firestone brand tires. After testing at the same optimized conditions described in Example 1 above, (40 minutes and 4000 g) the rubber was analyzed by both optical microscope and SEM in order to take images of the amount of tread worn off the surface ($\Delta H$ in mm). A sample SEM image for measuring $\Delta H$ is shown in FIG. 6. The SEM images were taken from cross sections of sample that were mounted on a SEM sample holder and coated with gold. The imaging was performed with a Cambridge Stereoscan 360 SEM interfaced with Oxford INCA software (conventional software for this purpose) at 40Δ magnification. The optical images for $\Delta H$ (in mm) were taken using the same setup as described in Example 1. The wear rate (mg/min) was then calculated using the equations listed below: $\Delta W/T$, where T=time, $\Delta W = \rho \times \Delta V$, $\rho$=density of the section, $\Delta V = L \times W \times \rho \times \Delta H$, L=length of the section, W=width of the section, $\Delta H$=thickness of the section before abrasion−thickness of the section after abrasion, where L=134.66 mg, W=7.5 mm, $\rho$=1.5 g/cm³. The test was run for 40 minutes under a normal force (hanging weight) of 40 Kg (applied where/how) Normal Force=hanging weight (Kg)×gravity constant (meters/second).

As shown in Table 3, the wear rate is calculated for each sample tested with the test method of the present invention. A wear rate index is generated for each sample by the following formula—Control Wear Rate divided by Experimental Wear Rate multiplied by 100—where Control Wear rate is that of sample H and Experimental Wear Rate is that of sample H, I, J, and K respectively. The control wear rate index is equal to 100 and a higher Test Index (present invention) refers to improved resistance to abrasion. As shown in the table, the wear rate index according to the test method of the present invention agrees with the actual outdoor wear rate index from taxi testing in Japan and the actual indoor wear results of tread weight loss index from conventional drum wear testing as previously described in Example 1.

TABLE 3

| Tire Tread → | H | I | J | K |
| --- | --- | --- | --- | --- |
| $\Delta H$ (mm) @ 40 min, 4 Kg | 0.2863 | 0.2664 | 0.2581 | 0.2848 |
| Wear Rate (mg/min) @ 40 min, 4 Kg | 0.1084 | 0.1009 | 0.0978 | 0.1079 |
| Indoor Weight Loss Index: | 100 | 101 | 105 | 103 |
| Outdoor Weight Loss Index: | 100 | 105 | 107 | 109 |

This measurement of wear/abrasion pattern and wear rate has resulted from a novel optimized test method. The method allows for rubber compounds such as tread to be compared from actual tires, including competitors, independent of tire construction and tire design differences. The optimized method involves testing for a shortened period of time under weight conditions, and slip—with no talc. The wear patterns are shown to accurately reproduce actual tire wear patterns from whole tire testing. The wear rates are shown to accurately reproduce the actual tire wear rates from indoor and outdoor whole tire testing. Thus in addition to greater accuracy, in less time, using samples off of actual tires, there is also a reduction in resources, including materials, required to obtain the improved results.

Thus, the scope of the invention shall include all modifications and variations that may fall within the scope of the attached claims. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of measuring wear rate in a rubber tire comprising, cutting a section of rubber out of the tire below the surface of the tire, measuring thickness of the section before abrasion of the section, attaching the section to the surface of a first wheel having an axis, attaching an abrasive substance, which is coated or laminated onto a substrate, to the surface of a second wheel having an axis, the first wheel having a diameter 3 to 6 times the diameter of the second wheel, rotating the two wheels under a load normal to the axes of the two wheels for a predetermined time, in opposite directions, in contact with each other, at uneven velocities resulting in slippage between the surfaces of the two wheels, wear including a wear pattern in the rubber section of the tire, and abrasion of the section, measuring thickness of the section after abrasion of the section, and measuring the wear rate of the rubber section of the tire based on changes in the section over time by using the formula $\Delta W/T$, where T=time, $\Delta W = \rho \times \Delta V$, $\rho$=density of the section, $\Delta V = L \times W \times \rho \times \Delta H$, L=length of the section, W=width of the section, $\Delta H$=thickness of the section before abrasion−thickness of the section after abrasion.

2. The method of claim 1, wherein optical images of the wear pattern of the tire section are periodically taken after wheel rotation and compared with optical images of the wear pattern of whole tires to match the wear patterns of the tire section and the whole tire.

3. The method of claim 1, wherein the time of rotation is stopped when the wear pattern of the section matches the wear pattern of the whole tire.

4. The method of claim 3 wherein the rotation is stopped at about 40 minutes.

5. The method of claim 2, wherein the optical images are taken at about 10 minute intervals.

6. The method of claim 1 wherein the slippage is up to about 70%.

7. The method of claim 1 wherein the slippage is about 10%.

8. The method of claim 1, wherein a ratio of diameter of the first wheel to the second wheel is about 3.5/1.

9. The method of claim 1, wherein a ratio of diameter of the first wheel to the second wheel is about 5.3/1.

10. The method of claim 1 wherein the load is about 500 grams to about 8 kilograms.

11. The method of claim 10 wherein the load is about 4 kilograms.

12. The method of claim 1 wherein the width of the wheels is about 8 mm to about 5 cm.

13. A method of measuring the wear rate in a rubber tire comprising, cutting a rectangular section of rubber out of the tire below the surface of the tire, measuring thickness of the section before abrasion, adhering the section to the surface of a first wheel about 173 mm in diameter and about 22 mm in width, adhering an abrasive substance to the surface of a second wheel about 49 mm in diameter and about 8.5 mm in width, rotating the two wheels for approximately 40 minutes, in opposite directions, in contact with each other, under a normal load of approximately 4000 g, at uneven velocities resulting in slippage between the surfaces of the two wheels of about 10% and abrasion of the section, measuring thickness of the section after abrasion, and measuring the wear rate of the rubber tire based on the formula $\Delta W/T$, where T=time, $\Delta W = p \times \Delta V$, p=density of the section, $\Delta V = L \times W \times p \times \Delta H$, L=length of the section, W=width of the section, $\Delta H$=thickness of the section before abrasion−thickness of the section after abrasion.

* * * * *